(12) United States Patent  
Arndt

(10) Patent No.: US 6,474,332 B2
(45) Date of Patent: Nov. 5, 2002

(54) BITE BLOCK

(75) Inventor: George A. Arndt, Madison, WI (US)

(73) Assignee: Wisconsin Medical Incorporated, Madison, WI (US)

( * ) Notice: Subject to any disclaimer, the term of this patent is extended or adjusted under 35 U.S.C. 154(b) by 0 days.

(21) Appl. No.: 09/164,928

(22) Filed: Oct. 1, 1998

(65) Prior Publication Data

US 2001/0015206 A1 Aug. 23, 2001

Related U.S. Application Data

(60) Provisional application No. 60/060,887, filed on Oct. 3, 1997.

(51) Int. Cl.$^7$ ............................................. A61M 16/00
(52) U.S. Cl. ............................... 128/200.26; 128/206.29
(58) Field of Search ................. 128/207.14, 200.26, 128/201.26, 206.29, DIG. 26, 848, 860, 859, 207.17

(56) References Cited

U.S. PATENT DOCUMENTS

| | | | | | |
|---|---|---|---|---|---|
| 1,498,810 A | * | 6/1924 | Poe | ...................... | 128/200.26 |
| 2,127,215 A | * | 8/1938 | Gwathmey | ............. | 128/207.14 |
| 2,599,521 A | * | 6/1952 | Berman | ................. | 128/207.14 |
| 2,786,469 A | * | 3/1957 | Cohen | ................... | 128/200.26 |
| 2,894,510 A | * | 7/1959 | Bellamy, Jr. | | |
| 3,088,466 A | * | 5/1963 | Nichols | ................. | 128/200.26 |
| 3,306,298 A | * | 2/1967 | Raimo | ................... | 128/207.14 |
| 3,568,680 A | * | 3/1971 | Raimo | ................... | 128/207.14 |
| 3,576,187 A | * | 4/1971 | Oddera | .................. | 128/207.14 |
| 3,587,589 A | * | 6/1971 | Ebner | ................... | 128/207.14 |
| 3,756,244 A | | 9/1973 | Kinnear et al. | | |
| 3,774,616 A | * | 11/1973 | White et al. | ........... | 128/200.26 |
| 3,908,665 A | * | 9/1975 | Moses | .................. | 128/207.14 |
| 3,926,196 A | * | 12/1975 | Bornhorst et al. | ..... | 128/207.14 |
| 3,930,507 A | * | 1/1976 | Berman | ................. | 128/207.14 |
| 4,068,658 A | * | 1/1978 | Berman | ................. | 128/200.26 |
| 4,069,820 A | * | 1/1978 | Berman | ................. | 128/200.26 |

(List continued on next page.)

OTHER PUBLICATIONS

Asai, T. and Morrison, S., "The Laryngeal Mask Airway: Its Features Effects and Role", *Can. J. Anaesth.* 41:10:930–60 (1994).

Khoo, S.T., "The Laryngeal Mask Airway–An Unusual Complication", *Anaesthesia and Intensive Care*, 21:2:249–50 (1993).

Marks, L.F., "Protection of The Laryngeal Mask Airway", *Anaesthesia*, 45:259 (1990).

Pennant, J.H. and White, P.F., "The Laryngeal Mask Airway: Its uses in Anaesthesiology", *Anaesthesiology*, 79:144–163 (1993).

Squires, S.J., Fragmented Laryngeal Mask Airway:, *Anaesthesia*, 47:274 (1992).

Vickers, et al., "Problem With The Laryngeal Mask Airway", *Anaesthesia*, 47:639 (1992).

Worsley, M.H. and Howie, C.C.M., Fixation of the Laryngeal Mask Airway:, *Anaesthesia*, 45:1001 (1990).

*Primary Examiner*—Aaron J. Lewis
(74) *Attorney, Agent, or Firm*—Quarles & Brady LLP

(57) ABSTRACT

A bite block for use with an airway conduit comprises an elongated arcuate body having a U-shaped channel defined therein and at least one end flange at a proximal end of the arcuate body, wherein the U-shaped channel corresponds in shape to a predetermined shape of a tubular conduit of an airway such as a laryngeal mask airway and to a human oral-pharyngeal cavity. The U-shaped channel is open to the lingual surface and can be inserted over a tubular conduit of a properly inserted laryngeal mask airway.

11 Claims, 2 Drawing Sheets

U.S. PATENT DOCUMENTS

| | | | |
|---|---|---|---|
| 4,166,467 A | | 9/1979 | Abramson |
| 4,211,234 A | * | 7/1980 | Fisher .................. 128/200.26 |
| 4,256,099 A | * | 3/1981 | Dryden ................ 128/200.26 |
| 4,270,531 A | * | 6/1981 | Blachly ................ 128/207.14 |
| 4,338,930 A | * | 7/1982 | Williams ............... 128/200.26 |
| 4,351,331 A | | 9/1982 | Gereg |
| 4,363,320 A | * | 12/1982 | Kossove ............... 128/200.26 |
| 4,425,911 A | | 1/1984 | Luomanen et al. |
| 4,495,945 A | | 1/1985 | Liegner |
| 4,553,540 A | * | 11/1985 | Straith ................. 128/207.14 |
| 4,896,667 A | | 1/1990 | Magnuson et al. |
| 4,919,126 A | * | 4/1990 | Baildon ................ 128/207.14 |
| 5,024,218 A | * | 6/1991 | Ovassapian et al. ... 128/200.26 |
| 5,205,281 A | * | 4/1993 | Buchanan ............. 128/207.14 |
| D348,099 S | | 6/1994 | Terrian |
| 5,355,874 A | * | 10/1994 | Bertram ................ 128/200.26 |
| 5,590,643 A | * | 1/1997 | Flam .................... 128/200.26 |
| 5,649,534 A | * | 7/1997 | Briggs, III ............ 128/207.14 |
| 5,655,519 A | | 8/1997 | Alfrey |
| 5,829,430 A | * | 11/1998 | Islava ................... 128/200.26 |
| 5,894,840 A | * | 4/1999 | King .................... 128/200.26 |

\* cited by examiner

BITE BLOCK

CROSS-REFERENCE TO RELATED APPLICATIONS

This application claims the benefit of provisional application Ser. No. 60/060,887, filed on Oct. 3, 1997.

STATEMENT REGARDING FEDERALLY SPONSORED RESEARCH OR DEVELOPMENT

Not applicable.

BACKGROUND OF THE INVENTION

The present invention relates generally to a medical device, and more particularly, to a bite block for use with a tubular airway. The invention can be used to prevent a critically ill or anesthetized subject or patient from inadvertently biting, disrupting, restricting or obstructing the airway.

A patient receiving medication under general anesthesia typically requires an artificial tubular airway or conduit from the external environment, through the mouth and pharynx, to the tracheobronchial tree opening. Common artificial tubular airways are the cuffed endotracheal tube and the laryngeal mask airway ("LMA"). The LMA includes three major components, namely (1) a generally triangular mask having an opening defined by an inflatable cuff that, in use, surrounds the glottic opening, (2) an airway connector for connection to an external mechanical ventilator or anesthesia machine, and (3) an arcuate tubular airway conduit corresponding in shape, size and radius to a human pharynx and oral cavity connected at one end to the mask and at a second end to the airway connector. The LMA device can be sized and shaped to conform to pediatric, juvenile or adult anatomy and is commercially available in several sizes to match clinical needs. The airway connector end of the LMA is referred herein to as the proximal end, while the mask end is referred to as the distal end.

The LMA can be disposable or reusable. The reusable plastic (e.g., silicone plastic) device can be reprocessed by high temperature steam autoclaving. With multiple cycles the mechanical properties of the plastic can be altered. The plastic can become brittle and prone to fracture under stress such as biting and potential severe patient harm from airway loss.

With the mask opening oriented toward the glottic opening, the mask is advanced past the teeth or gums and into the oral cavity of an anesthetized patient until resistance is encountered, thereby placing the distal end of the LMA in the cone shaped upper esophageal sphincter and the body of the mask over the glottic opening. The cuff is inflated to seal the glottic opening off from the surrounding tissue and to form a sealed conduit from the patient airway to the external environment. In use, the tubular conduit traverses the oral cavity and the teeth or gums. Patients undergoing general anesthesia with an LMA in place do not typically receive muscle relaxants or paralytic agents.

For proper LMA function, the tubular conduit must remain patent to the external environment at all times during use. Any process that obstructs or disrupts the tubular conduit is life threatening, as the patient is unconscious, the airway reflexes are obtunded, and ventilation is not otherwise possible. The passage of oxygen to the patient is reduced or eliminated. One such process is the involuntary patient response of biting or bringing the upper and lower teeth together in response to painful surgical stimuli such as cutting open the skin.

U.S. Pat. No. 3,756,244 (Kinnear and Havstad) discloses an elongated arched conduit that can be inserted into the mouth to act as an airway. This device is inserted next to, but does not surround, the tubular conduit. The width of the airway is also less than the diameter of the tubular conduit, so the conduit can be partially obstructed during involuntary biting. Using this device, it can be difficult to place other tubes and catheters as the oral cavity is occupied by two devices placed side by side. Several tubes are often inserted into the oral cavity during anesthesia for additional monitoring or drainage of the stomach.

U.S. Pat. No. 4,425,911 (Luomanen and Luomanen) is a bite block having a central rectangular channel and a pair of open channels on either side of the central channel. The central channel is not indexed to the diameter of an airway tubular conduit. Accordingly, the cross sectional area required to place the bite block and reliably prevent LMA obstruction is not minimized. The rectangular central channel is not long enough to push the tongue forward to prevent airway obstruction after the airway conduit is removed.

U.S. Pat. No. 4,495,945 (Liegner) discloses a bite block through which tubing or other apparatus can be inserted into the oral cavity.

BRIEF SUMMARY OF THE INVENTION

The foregoing problems are solved and a technical advance is achieved in a bite block for preventing obstruction of a tubular conduit of an airway. When properly utilized in the oral cavity of a patient, the bite block will prevent the patient from obstructing the tubular conduit by biting. The bite block is particularly applicable for use in conjunction with a laryngeal mask airway of the type described in U.S. Pat. Nos. 4,509,514 and 4,995,388.

The bite block of the present invention generally corresponds in cross-sectional profile to the shape of a human oral-pharyngeal cavity, which can be described by an arc of a circle of a defined radius. The bite block includes a U-shaped channel that corresponds in size and shape to the predetermined curved tubular portion of an appropriate sized tubular conduit. The U-shaped channel is of slightly greater diameter, width, and height than the predetermined diameter of the tubular conduit so that, in use, the U-shaped channel is in substantial apposition to the tubular conduit on three sides. The cross-sectional shape of the U-shaped channel is generally hemicircular, with a radius slightly exceeding the outer predetermined radius of the corresponding tubular conduit. Substantially parallel sides of the U-shaped channel extend from the maximal diameter of the hemicircle, and are longer than the outer predetermined radius of the corresponding tubular conduit.

The bite block is placed in a patient by opening the mouth and placing the bite block over the installed tubular conduit with minimal or no manipulation of the tongue or conduit. The bite block covers and surrounds the tubular conduit as it transits the teeth and oral-pharyngeal cavity, and has sufficient length to push the tongue forward.

A feature of the present invention is that the bite block is adapted in size and shape to fit into the human oral-pharyngeal cavity, thereby minimizing the cross-sectional area of the bite block in the patient airway.

Another feature of the present invention is that the bite block can fit snugly on a tubular conduit of predetermined size and shape.

Still another feature of the presented invention is that the bite block is sufficiently long at the distal end to push the tongue forward and thereby prevent the tongue from obstructing the patient's airway when no tubular conduit is in place.

An advantage of the present invention is that the bite block can be placed over an installed tubular conduit and can be positioned with little or no manipulation of the conduit or the patient's tongue.

Another advantage of the present invention is that the bite block can be placed or removed without disconnecting a pre-placed tubular conduit from an external device such as a mechanical ventilator or an anesthesia machine.

Yet another advantage of the present invention is that it can be injection molded of a thermoplastic material in a single-cavity mold, thereby reducing the cost and complexity of manufacture.

Other objects, features and advantages will become apparent from the detailed description and annotated drawing of the presently preferred embodiment.

DETAILED DESCRIPTION OF THE INVENTION

Referring now to FIGS. 1–5, a bite block 10 for use with a tubular conduit is shown, the bite block having proximal and distal ends, relative to the position of the device in a human patient's mouth, the proximal end contacting the oral opening, the distal end being inserted into the patient's throat. Although the bite block of the present invention can be used in conjunction with various airway devices, the preferred embodiment is preferably used in conjunction with a laryngeal mask airway (LMA) having a mask, an airway connector and a tubular conduit, as described in the Background.

Figure 3:
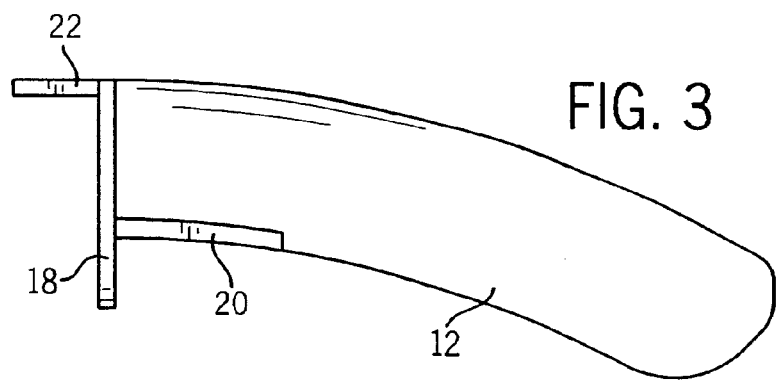
FIG. 3 depicts a side view of the bite block of FIG. 1.
Figure 5:
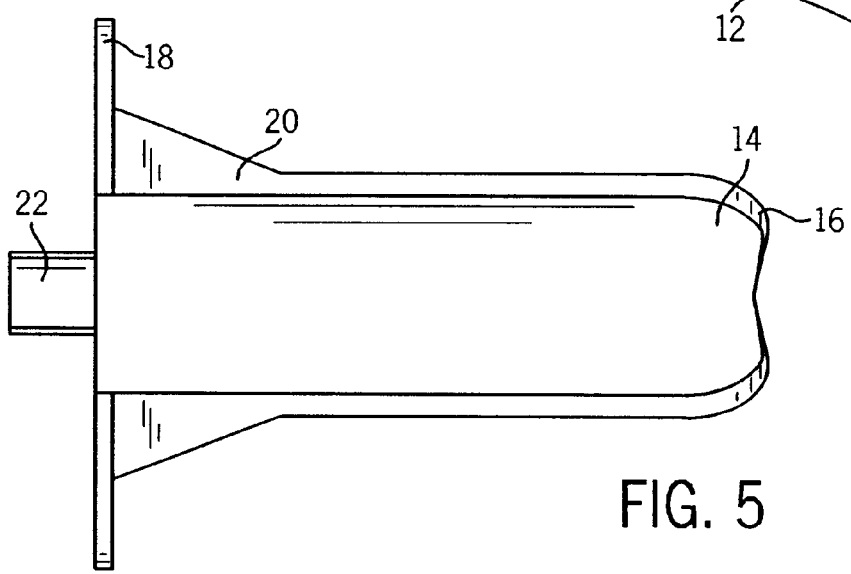
FIG. 5 depicts a bottom view of the bite block of FIG. 1.

The bite block 10 has an elongated, arcuate body 12 that corresponds in shape and size, when viewed in cross-section in a sagittal plane, to a human oral-pharyngeal cavity, as is best shown in the side view of FIG. 3.

Formed into the body 12 is a U-shaped wall 14 having a generally hemicircular surface and a pair of substantially parallel side surfaces extending from a diameter of the hemicircular surfaces. By "generally hemicircular," the applicant intends that the wall can comprise a smooth curved surface or can comprise a plurality of angled flat surfaces that confer an generally hemicircular shape to the wall. The wall 14 defines an elongated U-shaped channel when viewed in cross-section in a frontal plane. The channel, open along its length and at the proximal and distal ends of the body 12, is adapted in size and shape to receive therein a tubular conduit of an LMA airway. The U-shaped channel is preferably centrally disposed on the longitudinal axis of the bite block. The hemicircular surface of the wall 14 has a diameter larger than, and preferably only slightly larger than, the outer diameter of the tubular conduit. The sides of the wall 14 begin at a diameter of the hemicircle and are longer than, preferably only slightly longer than, the outer radius of the tubular conduit. When viewed from the side in cross-section, as in FIG. 6, the body and the U-shaped channel are shaped so as to generally correspond to the shape of the human oral-pharyngeal cavity and to the shape of an LMA tubular conduit.

The thickness of the channel wall 14 (shown as edge 16) can be constant or can vary across the length of the body 12, but should provide the body 12 with sufficient rigidity that, in use, a patient cannot obstruct the tubular conduit seated in the U-shaped channel. Although the channel defined by the wall 14 can be larger in length or width than the tubular conduit, it is preferred that the wall 14 and the conduit be in substantial apposition along the full length of the body 12.

At least one end flange 18 that can function as an outer boundary of the bite block 10 depends generally outward from the proximal end of the body 12. The end flange or flanges 18 are sufficiently large that, in use, they prevent a patient from swallowing the bite block 10. For security, at least two end flanges 18 are preferred. The end flange or flanges 18 preferably have rounded edges for patient comfort.

The bite block 10 can optionally include at least one support flange 20 that connects the at least one end flange 18 to the body 12. One support flange 20 per end flange 18 is preferred. The support flange or flanges 20 add rigidity and strength to the bite block 10 and can further prevent the tubular conduit from becoming obstructed.

The bite block 10 can also optionally include at least one gripping tab 22 attached to the proximal end of the body 12 or to an end flange 18, preferably attached to the body 12 between the end flanges 18. The optional gripping tab or tabs 22 is preferably sufficiently long so as to be conveniently gripped while positioning or removing the bite block 10 in the patient's mouth. The gripping tab 22 should also be preferably sufficiently short so as not to interfere with placing an anesthesia face mask onto a patient, if such a mask is used.

Figure 6:
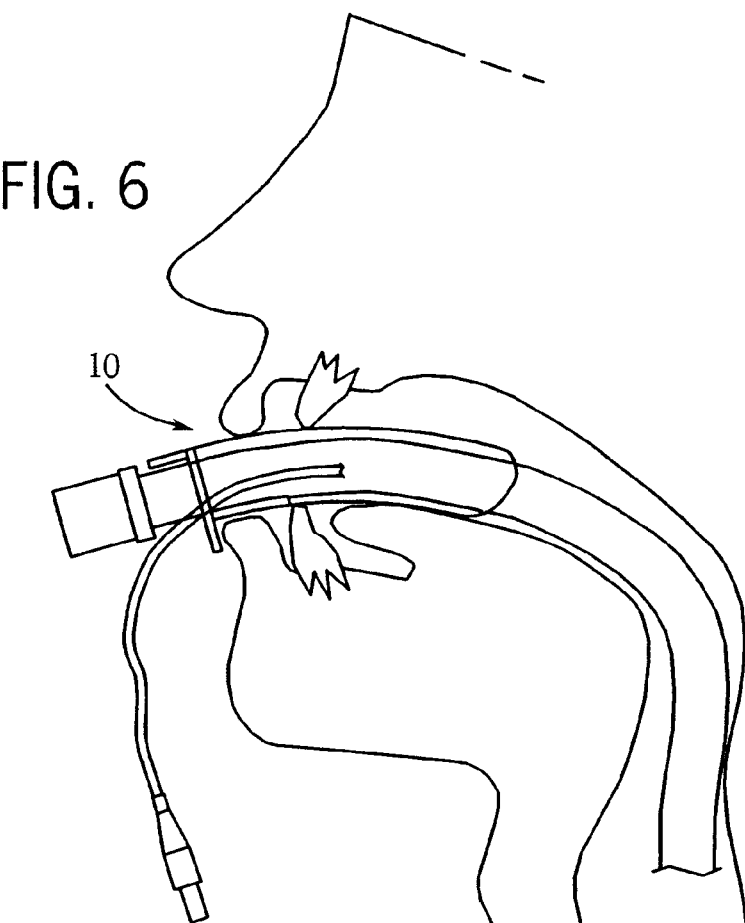
FIG. 6 depicts a cross-sectional view of the bite block of FIG. 1 in use.
Figure 1:
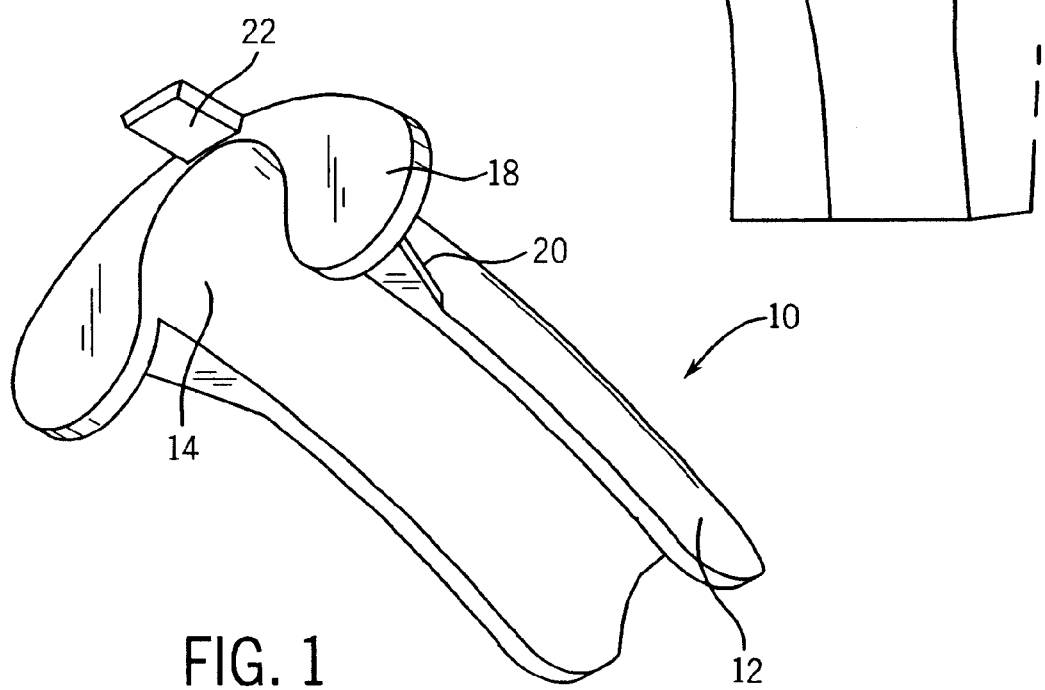
FIG. 1 depicts a perspective view of a bite block according to the present invention.
Figure 2:
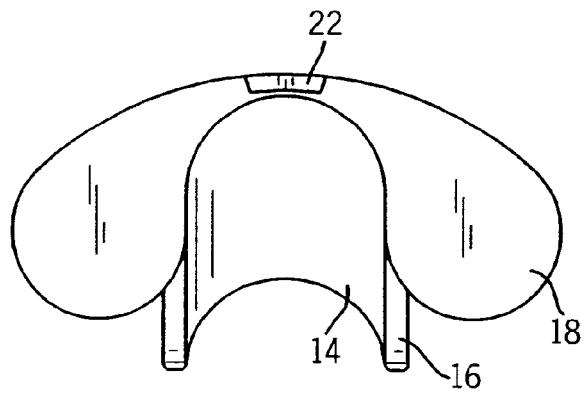
FIG. 2 depicts a frontal perspective view of the bite block of FIG. 1.
Figure 4:
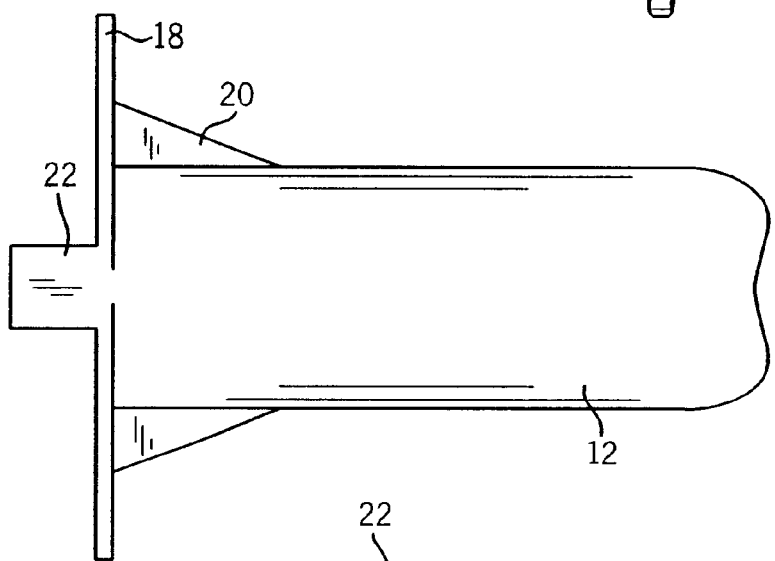
FIG. 4 depicts a top view of the bite block of FIG. 1.

FIG. 6 depicts the bite block 10 in use in conjunction with an LMA. The bite block is installed by opening the patient's mouth and advancing the wall 14 that defines the U-shaped channel over the LMA, preferably by holding optional gripping tab 22 and advancing the bite block 10 until the end flange or flanges 18 abuts against the skin of the oral opening and the wall 14 surrounds and is preferably in substantial apposition with the tubular portion of the LMA. The proximal portion of the bite block 10 between the upper jaw and lower jaw, including any optional support flange or flanges 20, prevents the patient from obstructing the tubular conduit.

Thus, it can be appreciated that the bite block 10 thus described can prevent involuntary obstruction of the tubular conduit of an LMA.

The present invention is not intended to be limited to the preferred embodiment disclosed herein, but rather to encompass all such modifications and variations as come within the scope of the appended claims.

I claim:

1. A bite block comprising:
an elongated arcuate body corresponding in shape to an oral-pharyngeal cavity and having proximal and distal ends relative to an oral cavity, the body comprising a wall having a hemicircular upper surface and a pair of substantially parallel side surface's, each side surface extending downward from a diameter of the hemicircular surface to a bottom edge, each bottom edge being substantially curved between the proximal and distal ends of the body, the wall extending from the proximal end to the distal end amd being open at the proximal and distal ends and defining, in cross section, an unenclosed and substantially U-shaped channel centrally disposed on a longitudinal axis of the body and adapted in shape and size to receive therein and under the hemicircular surface a tubular conduit having a preselected outer radius and diameter, the diameter of the hemicircular surface being greater than the outer diameter of the tubular conduit; and at least one end flange at the proximal end, the end flange dimensioned so as to preclude the proximal end from entering the oral cavity.

2. A bite block as claimed in claim 1 further comprising at least one support flange contacting the body and the end flange.

3. A bite block as claimed in claim 2 wherein the bite block comprises two support flanges.

4. A bite block as claimed in claim 1 further comprising at least one gripping tab at the proximal end.

5. A bite block as claimed in claim 1 wherein the bite block is a unitary construction.

6. A bite block as claimed in claim 1 wherein the arcuate body corresponds in shape to a human oral-pharyngeal cavity described by an arc of a circle having a defined radius.

7. A bite block comprising:

an elongated arcuate body corresponding in shape to an oral-pharyngeal cavity and having proximal and distal ends relative to an oral cavity, the body comprising a wall having a hemicircular upper surface and a pair of substantially parallel side surfaces, each side surface extending downward from a diameter of the hemicircular surface to a bottom edge, each bottom edge being substantially curved between the proximal and distal ends of the body, the wall extending from the proximal end to the distal end and being open at the proximal and distal ends and defining, in cross-section, an unenclosed and substantially U-shaped channel centrally disposed on a longitudinal axis of the body and adapted in shape and size to receive therein and under the hemicircular surface a tubular conduit having a preselected outer radius and diameter, the diameter of the hemicircular surface being greater than the outer diameter of the tubular conduit;

at least one end flange at the proximal end, the end flange dimensioned so as to preclude the proximal end from entering the oral cavity;

at least one support flange contacting the body and the end flange; and at least one gripping tab at the proximal end.

8. A bite block as claimed in claim 7 wherein the bite block comprises two support flanges.

9. A bite block as claimed in claim 7 wherein the bite block is a unitary construction.

10. A bite block as claimed in claim 6 wherein the bite block is a unitary construction.

11. A method for positioning in an oral cavity of a subject a bite block having a substantially U-shaped channel and an end flange, the oral cavity containing a tubular conduit, the method comprising the steps of:

inserting the bite block with the channel being over and open to a lingual surface in the oral cavity; and advancing the bite block into the oral cavity with the channel surrounding the tubular conduit until the end flange abuts against the oral opening and the proximal portion of the bite block is positioned so as to prevent the subject from obstructing the tubular conduit.

\* \* \* \* \*